United States Patent [19]

LeVeen et al.

[11] Patent Number: 4,684,627

[45] Date of Patent: Aug. 4, 1987

[54] TREATMENT OF CANCER WITH PHLORIZIN AND ITS DERIVATIVES

[76] Inventors: Harry H. LeVeen, 321 Confederate Cir., Charleston, S.C. 29407; Eric G. LeVeen, 358 Summit Ave., Mount Vernon, N.Y. 10552; Robert F. LeVeen, 312 Lombard St., Philadelphia, Pa. 19147

[21] Appl. No.: 640,170

[22] Filed: Aug. 13, 1984

Related U.S. Application Data

[63] Continuation-in-part of Ser. No. 300,136, Sep. 8, 1981, abandoned.

[51] Int. Cl.⁴ .............................................. A61K 31/70
[52] U.S. Cl. ...................................... 514/25; 536/4.1; 536/18.1; 536/18.2
[58] Field of Search .................. 514/25; 536/4.1, 18.1, 536/18.2

[56] References Cited

U.S. PATENT DOCUMENTS 3,523,937 8/1970 Biegeleisen ......................... 536/4.1

OTHER PUBLICATIONS

Kolber et al., "Chem. Abst.", vol. 67, 1967, P. 115099(q).
Ilinich et al., "Chem. Abst.", vol. 73, 1970, P 129240(q).
Floridi et al., "JNCL", vol. 66, No. 3, Mar. 1981, pp. 497–499.

*Primary Examiner*—Johnnie R. Brown
*Assistant Examiner*—F. T. Moezie
*Attorney, Agent, or Firm*—John S. Hale

[57] ABSTRACT

Phlorizin, its gluconuride and 4-deoxyphloretin-2-D-glucoside are used in treatment of cancer, particularly in combination with radio frequency thermotherapy and other modalities to accentuate the effect of such thermotherapy or other modality.

4 Claims, No Drawings

TREATMENT OF CANCER WITH PHLORIZIN AND ITS DERIVATIVES

This application is a continuation-in-part of copending application Ser. No. 300,136, filed by Harry H. LeVeen, Robert F. LeVeen and Eric G. LeVeen on Sept. 8, 1981, now abandoned.

This application relates to treatment of cancer and in particular provides a method of inhibiting the growth of tumors (cancer) cells by blocking glucose transport across the cell membrane.

Many cancer cells are characterized by their excessive glycolysis of glucose whereby glucose is converted to lactic acids (fermentation) whereas normal cells break glucose down to carbon dioxide and water (respiration) as described by Warburg in "The Metabolism of Tumors" published by Richard R. Smith Inc., New York, 1931. The rate limiting factor in this excessive tumor glycolysis is dependent on the rate at which glucose can be transported across the cell membrane. This had led some investigators to believe that the primary biochemical defect is the increased rate of glucose transport across the cell membrane. The intracellular transfer of glucose is directly related to the growth potential of the cancer cell. (J. Nat. Cancer Inst. 62: Jan. 3, 1979). Blocking of glucose transport across the cancer cell membrane deprives the cancer cell of its energy needs. The glucose analogue 5-thio-D-glucose, which blocks anaerobic glycolysis, has been shown by Kim et al, Science, Volume 200, pages 206 and 207 to sensitize tumor cells to heat which raises the metabolic rate and oxygen requirement of cancer cells as well as normal cells so that their energy requirements exceed their energy supply thus causing destruction of the cancer cell.

Phlorizin is a glucose, 1- [2-($\beta$D-glucopyranosyloxy)-4,6-dihydroxyphenyl]-3-(4-hydroxyphenyl)-1-propanone, which has been known and investigated both in humans and animals for many years, Benedict et al, Proceedings of the Society for Experimental Biology and Medicine, Volume 11, pages 134–136(1913–14). U.S. Pat. No. 3,523,937, issued Aug. 11, 1970, describes phlorizin analogues and their usefulness in the elimination of glucose from animals. Phlorizin is known to block the entry of glucose into cells, and it has now been found to be able to block glucose entry into cancer cells as well.

Cancer cells unlike normal cells require both glucose and oxygen to satisfy energy needs. The blocking of glucose entry impedes vital processes of the cancer cell and at elevated temperatures becomes lethal for cancer cells. By contrast, heat and the reduction of its glucose supply is well tolerated by normal tissues. Body tissue can satisfy energy needs by the metabolism of fatty acids in the presence of oxygen as the sole energy source. The oxygen tension in cancerous growths is extremely low and is inadequate for the metabolism of fat in cancer cells. Hence, the tumor derives most of its energy by the anaerobic breakdown of glucose to lactic acid.

SUMMARY OF THE INVENTION

In accordance with the invention, a process for the treatment of cancer in mammals is provided comprising administering phlorizin, its glucuronide or 4-deoxyphloretin-2-D-glucoside in an amount effective to inhibit glucose transport in the cancer cells. Such treatment of cancer is particularly effective while causing the body temperatures to be elevated either generally or locally in the region of the cancer. Such treatment is also effective in combination with other modalities including chemotherapy and radiation.

The invention is also directed to inclusion of Lonidamine, which has been found to have a synergistic effect with phlorizin and heat on cancer cells. Lonidamine and its effect as a selective inhibitor of aerobic glycolysis in murine tumor cells is described in J. Nat. Can. Inst. 66, page 497 (1981). The administration of phlorizin and lonidamine need not be simultaneous although this is preferred for ease of administration.

These compounds are effective in supressing the growth of cancer even in the absence of hyperthermia. The pharmaceutical composition according to the invention comprises phlorizin, its glucuronide or 4-deoxyphloretin-2-D-glucose together with a pharmaceutically acceptable carrier. These compositions may be solid or liquid and can be used in forms currently used in medicine such as tablets, capsules, syrups and injectable preparations. Because of its poor absorption, it is preferably administered parenterally dissolved in propylene glycol. Orally acceptable carriers are those currently used in medicine such as calcium carbonate, starch, lactose, talc, magnesium stearate, gum acacia, aqueous alcohol, glycol or oil solutions or suspensions.

The daily dosage to be administered depends on the lean body mass, diet and carbohydrate tolerance of subject in need of treatment. Generally, it has been found suitable to administer 200 mg to 1000 mg per kg of body weight per day of phlorizin or one of the above two derivatives with or without combination with lonidamine individual doses.

Excess phlorizin is excreted in the urine. Dosage of phlorizin required to effectively influence cancer is consequently easily determined since the patient acts as his own bioassay. In other words, a concentration of phlorizin which makes the tumor cells impermeable to glucose, makes all other cells all over the body impermeable to glucose cells.

How well glucose is prevented from entering the cancer cell can be assessed by measuring concentration of glucose in the urine. Urine is formed by glomerular filtration. The glomerular filtrate contains all the constituents of blood except protein. As the glomerular filtrate passes down the renal tubules, the proximal tubule reabsorbs glucose. Therefore, normal urine contains no glucose unless there is some impairment of reabsorption, such as occurs in diabetes mellitus. When the dosage of phlorizin is adeqate to prevent glucose entry into cells, the proximal tubular cells can no longer absorb glucose. Glucose will then appear in the urine almost at the same concentration that it is present in the serum. Hence, the effect of phlorizin on glucose metabolism can be monitored by the urinary concentration of glucose, and the correct dosage determined. A satisfactory concentration is achieved in the blood stream when all of the glucose clearances in the urine approaches the xylose or creatinine clearance. In man, the creatinine clearance can be used. Clinical experience has shown that approximately 100 mg's per kilo of body weight is intravenously required to completely phlorizinize the patient as evidenced by the failure of the tubular cells to absorb any glucose. The effects of phlorizin last approximately one to one and one-half hours when administered intravenously. A better means of administration is to inject the material at doses of approximately 500 mg's per kilo intramuscularly. Although the phlorizin can be given by mouth, it requires approximately 400 mg's per kilo to completely phlorizinixze the patient, and much of the dose appears in the stools. That glucose reabsorbtion in the kidney is completely blocked can be determined by comparing clearance of glucose to the clearance of xylose after the administration of xylose. The xylose clearance is determined by taking the concentration of xylose in the blood and measuring the total amount of xylose excreted (in a timed period) divided by the plasma concentration and the number of minutes of collection. This will determine how many cc's of blood were completely cleared each minute of xylose.

Xylose is a nonmetabolized sugar which is not reabsorbed by the tubules. The glucose clearance and the xylose clearance become identical when complete phlorinization has been obtained. Other substances can be used in place of xylose such as insulin or sorbitol. The clearance of these substances which are filtered but not secreted or reabsorbed is approximately 125 cc's per minute. This value is called the filtration rate since it is a measure of glomerulus filtration in one minute. The glucose clearance approaches 125 cc's per minute when the patient is completely phlorizined. This is easily determined by measuring the quantity of glucose excreted divided by the serum glucose concentration and the number of minutes over which the urine was collected. The urinary and serum glucose concentrations become close to one another, but the concentration in the urine is always higher, unless water reabsorbtion from the tubules is minimal, which can occur at high glucose concentrations. When the glucose clearance is identical to a substance that is filtered by the glomerulus but not secreted or reabsorbed by the tubules (such as insulin or xylose), the patient is completely phlorinized.

In practice the administration of 500 mg of phlorizin in propylene glycol or carbowax per kilo of body weight given intramuscularly is usually more than adequate dose in most patients. One need not fear giving an excessive quantity of phlorizin since this substance has proven to be relatively nontoxic and is rapidly excreted in the urine. The effect of phlorizin is dependent on a concentration in the extracted fluid which will completely block all of the receptors sites for glucose.

In animals or humans fed or injected with phlorizin, ketosis occurs and the respiratory quotient of the entire body shifts to that of fat becoming as low as 0.65. Nonetheless, glucose is still required for the metabolism of cancer cells, and hence the metabolism of tumor cells is selectively depressed. At this level the cancer cells are sensitized to treatment with heat and other modalities. The temperature of the cancer tissue can be raised by localized radiofrequency thermotherapy. Systemic hyperthermia is also very useful and can cause the destruction of large amounts of cancer tissue. Usually, only one dose of phlorizin is administered during heat therapy.

Treatment with phlorizin can also be effectively combined with treatment of cancer using Lonidamine. The Lonidamine is preferably administered at a dosage of about 50 mg to 500 mg per kilo of body weight per day.

Effective therapy can also occur without the application of heat by administration of phlorizin alone, or parenterally at levels of about 100 mg or more per kg of body weight per day.

When referring to phlorizin, above, and in the following description it should be understood that phlorizin glucuronide and 4-deoxyphloretin-2-D-glucoside can be substituted in equivalent amounts with comparable results.

A patient with lung cancer is treated with radiofrequency thermotherapy preceded by treatment with phlorizin in accordance with the present invention, as follows. The phlorizin is dissolved in ethylene glycol at a concentration of 500 mg per cc. After fasting overnight the patient is given 300 mg of phlorizin per kilo body weight intramuscularly which induces glycosuria. The urinary sugar reaches a maximum in about fifteen to twenty minutes at which point radiofrequency thermotherapy is commenced. R.F. treatment is continued to raise the tumor temperatures to approximately 44° C. The dose of phlorizin is repeated in three hours, and glycosuria persists for a total of eight hours. The glycosuria condition is used as an indicator to show that sufficient concentration of phlorizin has been reached in the tissue, on the assumption that the tumor cells are affected as the kidney cells and are also unable to transfer glucose. Treatment is repeated, as above, as required.

Phlorizin and the two derivatives can also be used to accentuate response to chemotherapy with drugs, such as adriamycin. These drugs are used after phlorizination as described above in connection with the use of radiofrequency thermotherapy.

We claim:

1. A method for the treatment of lung cancer in humans which comprises administering lonidamine and one or more compounds selected from the group consisting of phlorizin, phlorizin glucoronide and 4-deoxyphoretin-2-D-glucoside in an amount effective to inhibit glucose transport in the cancer cells while subjecting said cancer cells to additional therapy in the form of chemotherapy, thermal or radiation therapy.

2. The method of claim 1 wherein the dosage of said compounds is an effective amount for lung cancer treatment of at least 100 mg per day per kg of body weight and the dosage of lonidamine is 50 to 500 mg per kilo of body weight per day.

3. The method of claim 2 wherein the dosage of said compound is 200 to 1000 mg per kg of body weight per day.

4. The method of claim 1 wherein said lonidamine and said compound are administered with a pharmaceutically acceptable carrier.

* * * * *